United States Patent
Belfer

[19]

[11] Patent Number: 5,921,241
[45] Date of Patent: Jul. 13, 1999

[54] ANTI-SNORING DEVICE HAVING AN ADJUSTABLE EXTERNAL ORAL SHIELD

[76] Inventor: William A. Belfer, 804 W. Park Ave., Ocean, N.J. 07712

[21] Appl. No.: 09/110,214

[22] Filed: Jul. 6, 1998

Related U.S. Application Data

[60] Division of application No. 08/995,533, Dec. 22, 1997, and a continuation-in-part of application No. 08/609,617, Mar. 1, 1996, Pat. No. 5,720,302.

[51] Int. Cl.$^6$ ........................................................ A61F 5/56
[52] U.S. Cl. ............................ 128/848; 128/859; 602/902
[58] Field of Search ...................................... 128/846, 848, 128/859–862; 2/2; 602/902; 433/6

[56] References Cited

U.S. PATENT DOCUMENTS

| | | | |
|---|---|---|---|
| 3,692,025 | 9/1972 | Greenberg | 128/861 |
| 4,198,967 | 4/1980 | Dror | 128/860 |
| 4,495,945 | 1/1985 | Liegner | 128/200.26 |
| 4,944,947 | 7/1990 | Newman | 128/861 |
| 5,117,816 | 6/1992 | Shapiro | 128/848 |
| 5,365,946 | 11/1994 | McMillan | 128/861 |

*Primary Examiner*—Michael A. Brown
*Attorney, Agent, or Firm*—Ezra Sutton

[57] ABSTRACT

An anti-snoring device including a moldable dental overlay for covering the lower teeth of the user and for maintaining the tongue in contact with the palate to prevent air flow from causing the palate to reverberate during mouth breathing; an extension member fixedly connected to the front of said dental overlay; a moldable oral shield worn outside the mouth and being conformable to the user's upper lip for preventing the lower jaw from drifting inferiorly and posteriorly during sleep; and a connecting member being slidably connected to the oral shield, and having an opening for slidably receiving said extension member. The anti-snoring device may be made of thermoplastic or elastomeric resin materials for moldability to the user's mouth.

14 Claims, 5 Drawing Sheets

ANTI-SNORING DEVICE HAVING AN ADJUSTABLE EXTERNAL ORAL SHIELD

This application is a division of application Ser. No. 08/995,533, filed Dec. 22, 1997, allowed.

This application is a continuation-in-part of application Ser. No. 08/609, 617, filed on Mar. 1, 1996, now U.S. Pat No. 5,720,302.

FIELD OF THE INVENTION

This invention relates to an anti-snoring device, and more particularly, to an anti-snoring device having an adjustable external oral shield which reduces air turbulence and promotes nasal breathing while sleeping to prevent the act of snoring.

BACKGROUND OF THE INVENTION

Snoring or sleep apnea is caused by the condition where the tongue relaxes and contributes to blocking of the air passageway in the pharynx or lingual compartment. Further, the loose tissue within the mouth cavity including the tongue, the pharyngeal folds, the soft palate, the muscularis uvulae and the palate-pharyngeal arch tend to vibrate as tidal air flows past during sleep which also causes snoring.

Anti-snoring devices are effective when they protract (pull or hold) the mandible (lower jaw) forward and upward and elevate the tongue, so that the tongue does not occlude the air passageway drifting inferiorly and posteriorly while sleeping. Most anti-snoring devices accomplish this aforementioned task by holding the lower jaw forward against a rigid dental component which is fixed to the upper teeth or to the upper and lower teeth. These anti-snoring devices fix the dental component from falling out of the mouth by clasping or biting of the user's teeth into the dental component and by close adaptation to the user's teeth. The primary disadvantages in using the above prior art devices, is that they require professional lab services for fitting of the anti-snoring device to the user's mouth. Such devices could cause irreversible changes in the bite of the user or permanently alter the jaw position of the user unless the anti-snoring device fitting is closely supervised by a dentist.

There is a need for an anti-snoring device that does not rigidly bind to the dental structures of the user's mouth and does not require professional supervision or assistance in its fabrication. In addition, the anti-snoring device should not pit the lower jaw against the upper jaw and should not alter the bite of the user. Further, an external oral shield should be used to hold the lower jaw from drifting inferiorly and posteriorly during is: sleep. The oral shield should be adjustable by the user, such that the device can be adjusted to fit various jaw sizes and bite relationships. Also, the device should include an intra oral dental overlay to support the tongue against the palate and keep the palate of the user's mouth from reverberating during mouth breathing.

DESCRIPTION OF THE PRIOR ART

Anti-snoring devices of various designs, appearances, styles and materials of construction have been disclosed in the prior art. For example, U.S. Pat. No. 2,178,128 to Waite discloses an anti-snoring device having a shield worn inside the mouth. This device does not have a contacting dental overlay. U.S. Pat. No. 4,169,473 to Samelson discloses an anti-snoring device having an oral shield, upper and lower dental overlays, and a tongue-receiving socket. This device is structurally and functionally different from the present invention.

The prior art patents do not teach or disclose the structure of the present invention of an anti-snoring device having an external, adjustable oral shield being worn outside the upper lip of the mouth, and which is removably connected by a connecting member and adjustable with regard to vertical height. In addition, the prior art does not disclose an oral shield that is slidably adjusted relative to the dental overlay along the length of the anterior handle.

Accordingly, the primary object of the present invention is to provide an anti-snoring device having an adjustable oral shield and a dental overlay connected by an anterior handle or extension member to reduce or eliminate nocturnal snoring.

Another object of the present invention is to provide an anti-snoring device that is easily self-adaptable and which eliminates the need for professional and laboratory assistance or clinical fabrication.

Another object of the present invention is to provide an anti-snoring device that is fabricated from a thermoplastic material (elastomeric resin) which is moldable in shape to the user's lower jaw and perioral structure.

Another object of the present invention is to provide an anti-snoring device which is moldable after immersion in boiling water so that it can be adapted by the user to have a comfortable and individualized fit.

Another object of the present invention is to provide an anti-snoring device that has an adjustable external oral shield structure which reduces air turbulence within the user's mouth and thus promotes nasal breathing to prevent the act of snoring.

Another object of the present invention is to provide an anti-snoring device that has an adjustable external oral shield structure which acts as an upper lip seal, such that the user is more apt to breath through the nose instead of the mouth to prevent the act of snoring.

Another object of the present invention is to provide an anti-snoring device that has an adjustable external oral shield which is reduced in size so that the anti-snoring device is more comfortable, less bulky, more aesthetic looking and is more acceptable for use by a patient.

Another object of the present invention is to provide an anti-snoring device that has an adjustable external oral shield which only contacts the tissue below the nose and the inferior border of the upper lip, such that the reduced size adjustable external oral shield still functions in preventing the lower jaw from moving inferiorly and posteriorly while the user is in the supine (sleeping) position.

Another object of the present invention is to provide an anti-snoring device that has an adjustable external oral shield consisting of two different copolymer resin layers that have dissimilar melting points such that the softening and molding of the layered oral shield in boiling water does not distort the extension member and connecting member nor impair the adjustability of the oral shield relative to the connecting member.

Another object of the present invention is to provide an anti-snoring device that has an extension member, a connecting member, and a backing layer for the oral shield which will maintain their shapes and dimensions after submersion in boiling water and concurrently allow the elastomeric layer of the oral shield to be softened and molded to the user's external subnasal and lip tissue.

Another object of the present invention is to provide an anti-snoring device that has an adjustable external oral shield that can be shaped to the user's external subnasal and lip tissue by manual manipulation of the oral shield without the immersion of the anti-snoring device into boiling water.

Another object of the present invention is to provide an anti-snoring device that has an adjustable external oral shield consisting of two layers, where the outer backing layer is made from a bendable metal or plastic; and the inner surface layer is made from an elastomeric material or a thermolabile copolymer resin. This construction allows the oral shield to be adapted to the upper lip contour of the user by bending and contouring with finger pressure instead of softening of the oral shield by the water boiling method.

Another object of the present invention is to provide an anti-snoring device that has an intra oral dental overlay structure which supports the tongue against the user's palate to keep the palate from reverberating during mouth breathing to prevent snoring by the user.

Another object of the present invention is to provide an anti-snoring device that includes an external oral shield in combination with an intraoral dental overlay connected by an anterior handle, such that the oral shield can be slidably adjusted on the handle by the user and which reduces the velocity of air flow through the mouth to reduce the reverberation of the palate to prevent the act of snoring. However, another method of adjusting the oral shield upon the extension member could employ reciprocal screws, a jack screw or other screw mechanisms.

A further object of the present invention is to provide an anti-snoring device which can be easily used, mass produced in an automated and economical manner, and is readily affordable by the user.

A still further object of the present invention is to provide an adjustability of the oral shield along the handle of the dental overlay, which will allow the device to accommodate individual differences in the upper and lower jaw relationships of users. The user is able to adjust the entire anti-snoring device comfortably without sophisticated procedures and professional help.

An even further object of the present invention is to provide an adjustability of the oral shield along the telescoping vertical section of the connecting member, which allows vertical height adjustment relative to the oral shield thereby allowing the oral shield to accommodate individual differences beneath the user's nose and upper lip relationships. The user is able to adjust the entire anti-snoring device comfortably without sophisticated procedures and professional help.

SUMMARY OF THE INVENTION

In accordance with the present invention, there is provided an improved anti-snoring device for controlling snoring during sleep. The anti-snoring device includes a moldable dental overlay for covering the lower teeth of the user and for maintaining the tongue in contact with the palate to prevent air flow from causing the palate to reverberate during mouth breathing; an extension member fixedly connected to the front of the dental overlay; a moldable oral shield worn outside the mouth and being conformable to the user's upper lip for preventing the lower jaw from drifting inferiorly and posteriorly during sleep; and a connecting member being slidably connected to the oral shield, and having an opening for slidable receiving the extension member. The anti-snoring device may be made of thermoplastic or elastomeric resin materials for moldability to the user's mouth.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED EMBODIMENT

Figure 1:
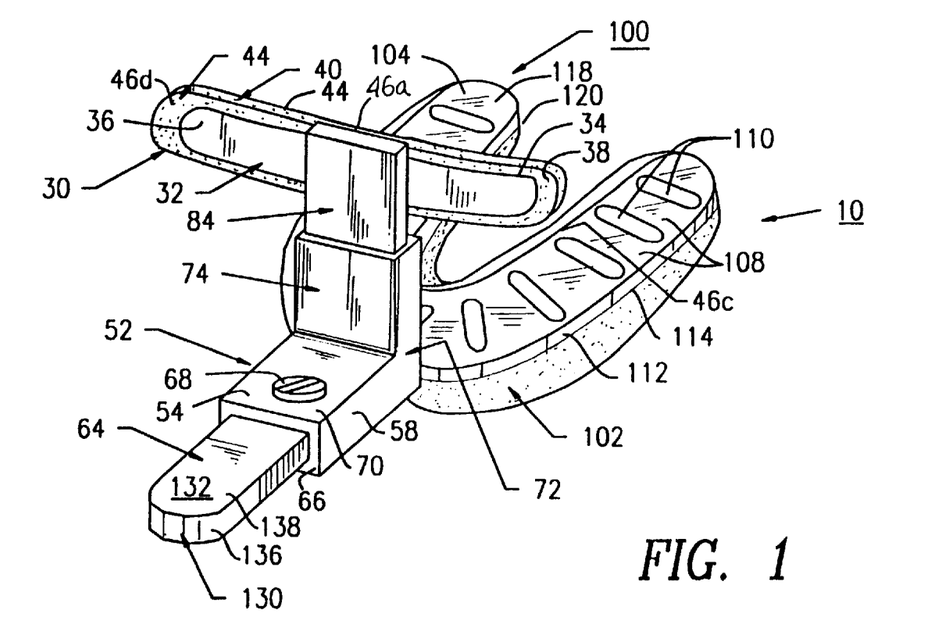
FIG. 1 is a front perspective view of the preferred embodiment of the present invention showing an anti-snoring device having an adjustable external oral shield, a connecting member with a set screw, and an intraoral dental overlay with an anterior handle attached thereto, and in an assembled configuration.
Figure 2:
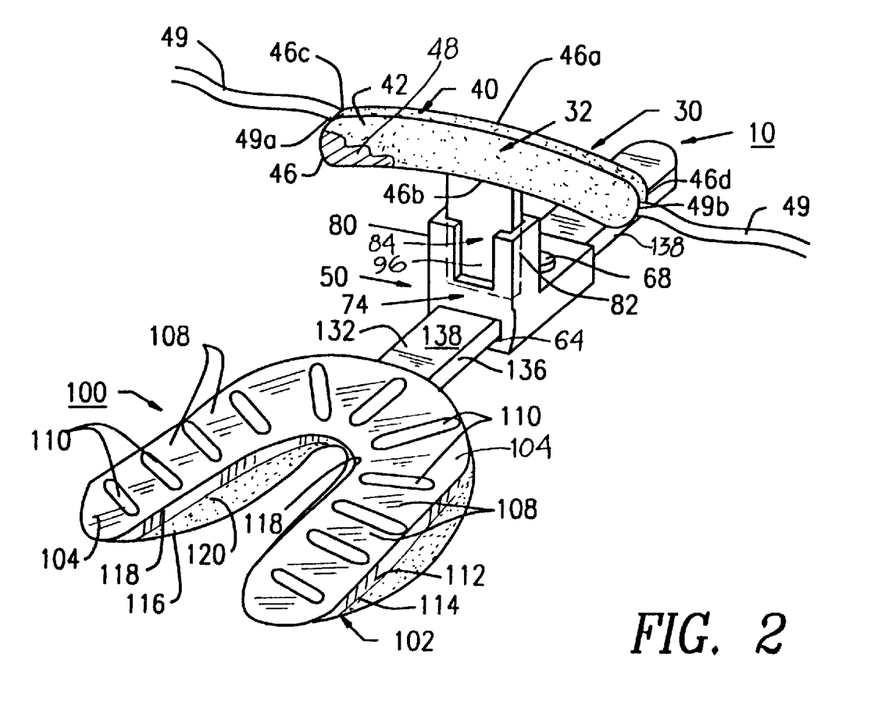
FIG. 2 is a rear perspective view of the preferred embodiment of the present invention showing an anti-snoring device having an adjustable external oral shield, a connecting member with a set screw, and an intraoral dental overlay with an anterior handle attached thereto, and in an assembled configuration.
Figures 3, 4:
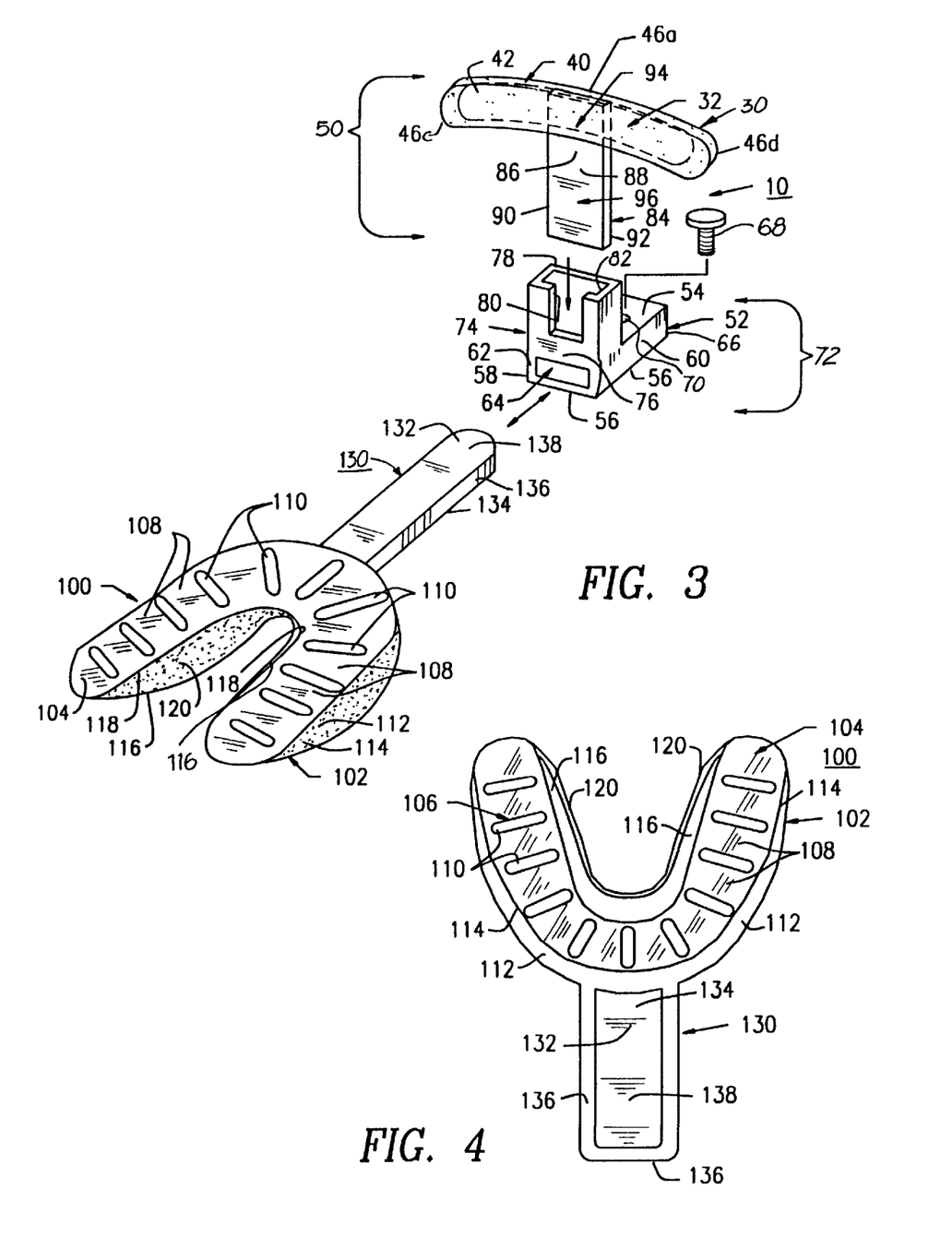
FIG. 3 is an exploded perspective view of the preferred embodiment of the present invention showing an anti-snoring device having an adjustable external oral shield, a connecting member with a set screw, and an intraoral dental overlay with an anterior handle attached thereto, and in an unassembled configuration.
FIG. 4 is a rear, bottom perspective view of the present 159 invention showing the intraoral dental overlay having an integrally attached anterior handle for inserting into the handle opening of the connecting member.

The anti-snoring device 10 and its component parts of the preferred embodiment of the present invention are represented in detail by FIGS. 1 through 6. The anti-snoring device 10 comprises an external, adjustable oral shield 30 being substantially elliptical and convex in shape; a connecting member 50 being substantially L-shaped in configuration; and an intraoral lower dental overlay 100 having an integrally attached anterior handle or extension member 130, as shown in FIGS. 1 to 3 of the drawings.

Oral shield 30, as shown in FIGS. 1 through 3, includes an outer backing layer 32 being a bendable metal or plastic, and an inner elastomeric material layer 40 being moldable and conformable to the upper lip 28u and subnasal tissue area of the user's mouth 26 after softening the elastomeric layer 40 in boiling water. The inner elastomeric material layer 40 is permanently attached to the outer backing layer 32. Outer backing layer 32 includes an inner surface wall 34, an outer surface wall 36 and perimeter edging 38. Inner elastomeric layer 40 includes an inner surface wall 42, an outer surface wall 44 and perimeter edges 46a, 46b, 46c, and 46d. Outer backing layer 32 is centrally located within the inner elastomeric material layer 40, such that the inner surface wall 34 of back layer 32 is permanently affixed to the outer surface wall 44 of elastomeric layer 40, as shown in FIGS. 1 to 3 of the drawings, thus forming a layered configuration for external oral shield 30. This construction allows the oral shield 30 to be adapted to the lip contours by bending and contouring the oral shield 30 with finger pressure with or without immersion of the oral shield 30 in boiling water for softening and moldability depending upon the types of layered materials used in the oral shield 30 construction.

The outer backing layer 32 is made from bendable metals selected from the group consisting of aluminum, copper, stainless steel, steel, and equivalents thereof or is made from bendable plastic selected from the group consisting of LEXAN®, PLEXIGLASS, NYLONS, KEVLAR, TEFLON and equivalents thereof.

The inner elastomeric material layer 40 is made from moldable and conformable elastomeric and thermolabile plastic materials selected from the group consisting of Sorbothane®, urethane foams, silicones, ethyl vinyl acetate, methyl vinyl acetate, methyl acrylate, other elastic copolymer resins and equivalents thereof. These aforementioned elastomeric and thermolabile plastic materials are softened and moldable in hot or boiling water, and will return to a hardened and stable form upon cooling to room temperature.

There are various fabrication combinations for the dual layered, external oral shield 30 that can be used for the anti-snoring device 10. The preferred structure of the external oral shield 30 is a double layer consisting of an outer metal backing strip layer 32 made of aluminum which is attached to the softer inner elastomeric material layer 40 made of Sorbothane®. Other elastomeric materials such as urethane, urethane foams, silicones, vinuls, copolymeter resins, are readily substituted for the Sorbothane® material for use with the metal backing strip layer 32. Thus, the elastomeric material layer 40 provides a protective layer upon the skin from the metal backing layer 32, as the elastomeric material is soft, comfortable and conformable to the configuration and contour of the metal strip layer 32. The resistance that the oral shield 30 provides to backward displacement to the lower jaw 12 does not cause irritation and bruising of the lip tissues 28, such that the elastomeric material layer 40 prevents the metal backing layer 32 from pinching or cutting into the skin tissues. The elastomeric material layer 40 does not have sufficient rebounding and cushioning effect to alter the jaw posture once the proper jaw posture has been established and the adjustable, external oral shield 30 has been fixed in its proper position.

Another fabrication combination of a dual layer structure for oral shield 30 includes an outer plastic backing strip layer 32 made of a thin, semi-rigid polycarboxalate resin such as LEXAN®. LEXAN® has a softening temperature of about 310° degrees F. which z will not readily deform in boiling water. The plastic backing U strip layer 32 is also attached to the elastomeric material layer 40 made of a thermolabile copolymer resin, such as ethylene vinyl acetate. An example of an ethylene vinyl acetate being commercially produced is ELVAX® by the DuPont Company. ELVAX® has a softening and molding temperature between 125° degrees F. to 175° degrees F. which becomes very soft in boiling water. The aforementioned plastic backing strip layer 32 of LEXAN® provides enough support to the aforementioned elastomeric material layer 40 of ELVAX®, such that when the elastomeric material layer 40 is softened in boiling water, the oral shield 30 can then be manipulated and mechanically contoured with finger pressure by the user. Thus, after the oral shield 30 is immersed in boiling water the elastomeric material layer 40 is softened and briefly cooled, and the elastomeric material layer 40 is then pressed against the upper lip 28u so that it will make an imprint of the lip contours. The plastic backing strip layer 32 of LEXAN® also gives rigidity and resistance to the oral shield 30, such that the oral shield 30 can resist deflection and distortion and resist the forces placed upon the anti-snoring device 10 by the repostured lower jaw 12 of the user.

Additionally, the oral shield 30 can have a double sided adhesive tape 48 attached to the inner surface wall 42 of the elastomeric material layer 40 or an elastic retention or retaining strap 49 attached at strap ends 49a and 49b to the perimeter edges 46c and 46d, respectively, of the elastomeric layer 40 by means of gluing or stitching as shown in FIG. 2. The oral shield 30 is held in place on the user's upper lip 28u by the adhesive tape 48 or is held in place on the user's head by the retention or retaining strap 49, thus preventing the expelling of the anti-snoring device from the user's mouth 26 by the patient involuntarily until he/she gets used to wearing the anti-snoring device 10.

The connecting member 50 includes a horizontal section 52 being integrally attached at the rear wall 66 to a telescoping vertical section 72, as shown in FIG. 3 of the drawings. The horizontal section 52 includes a top wall 54, a bottom wall 56, side walls 58 and 60, front and rear walls 62 and 66 having an extension member opening 64 extending therebetween for slidably receiving the extension member 130 therein. Top wall 54 includes a centrally located threaded set screw opening 70 for receiving a set screw 68 for holding the horizontal section 52 in place relative to a precise location on the extension member 130. When screw 68 is tightened it applies a frictional resistance against the elongated strip section 138 of the extension member 130 of the dental overlay 100 and thereby prevents the horizontal (yoke) section 52 and the oral shield 30 from moving from its set position.

The telescoping vertical section 72 includes a lower vertical extension member 74 having a front wall 76, a rear wall 78 and side channels 80 and 82 for slidably receiving an upper vertical extension member 84. The upper vertical extension member 84 includes a front wall 86, a rear wall 88, side walls 90 and 92, an upper end 94 and a lower end 96. The upper end 94 of front wall 86 of the upper vertical member 84 is permanently and centrally connected to the outer surface wall 36 of the metal backing layer 32 of oral shield 30, as shown in FIG. 1 of the drawings. The side walls 90 and 92 of the lower end 96 of the upper vertical member 84 are slidably received within the side channels 80 and 82, respectively, of the lower vertical member 74 for adjustability of the external oral shield 30. The sidewalls 90 and 92 of the upper wall member 84 stay in place by friction relative to the side channels 80 and 82, respectively, of the lower vertical member 74. Once the vertical member 74 can be positioned vertically it can be glued in place. The telescoping vertical section 72 of connecting member 50 allows for vertical height adjustment relative to the oral shield 30, thereby allowing the oral shield 30 to accommodate individual differences beneath the user's nose and upper lip 28u relationships. The user is able to adjust the entire anti-snoring device 10 comfortably without sophisticated procedures and professional help.

The extraoral shield 30 can be permanently fixed or stabilized upon the horizontal or vertical extension member 54 and 84, as shown in FIGS. 7, 8, 9, 10 by gluing, pop-riveting, stapling, crimping, screwing, or snapping the shield on to the extension members 54 or 84.

Furthermore, another means of adjusting the horizontal or vertical position of the extraoral shield 30 would be to utilize a jack screw component or screw attachment to the shield 30 and the extension member 84 so that the shield 30 is positioned appropriately upon the lip 28u.

The connecting member 50 and its component parts can be made of various types of plastics including carboxylate copolymer resins, nylons or ABS plastics. For example, when the elastomeric material layer 40 of the oral shield 30 is made from an ethylene vinyl acetate, the horizonal section 52 and the lower vertical extension member 74 and the upper vertical extension member 84 of connection member 50 are made from a carboxylate resin. This is done such that the upper vertical extension member 84 can be bonded to the outer surface wall 44 of elastomeric material layer 40 of the oral shield 30.

Figure 5:
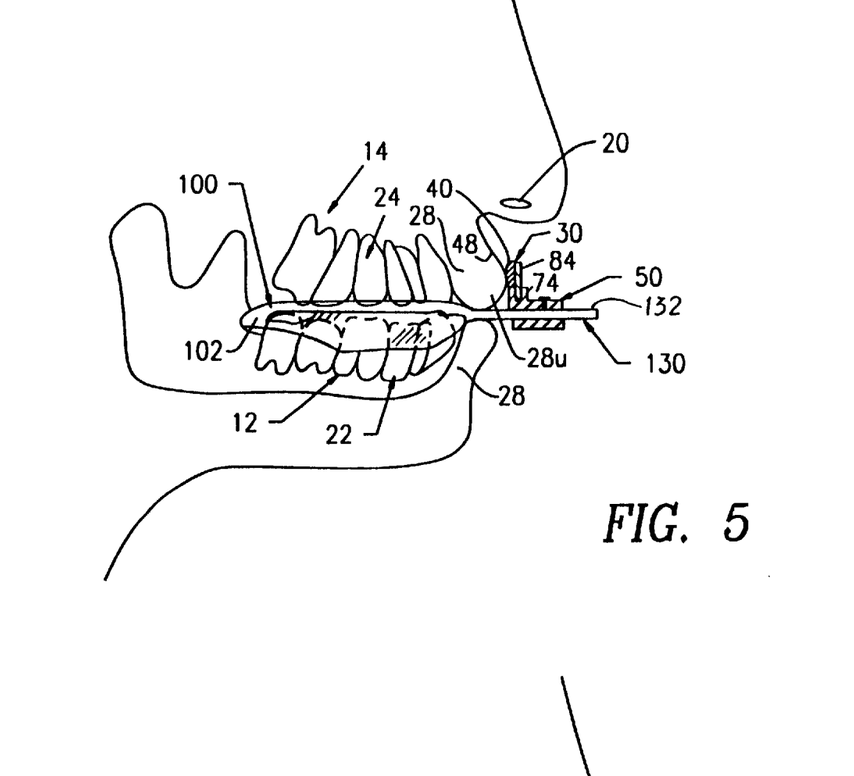
FIG. 5 is a cross-sectional view of the present invention showing the anti-snoring device inserted in the oral cavity of a user.
Figure 6:
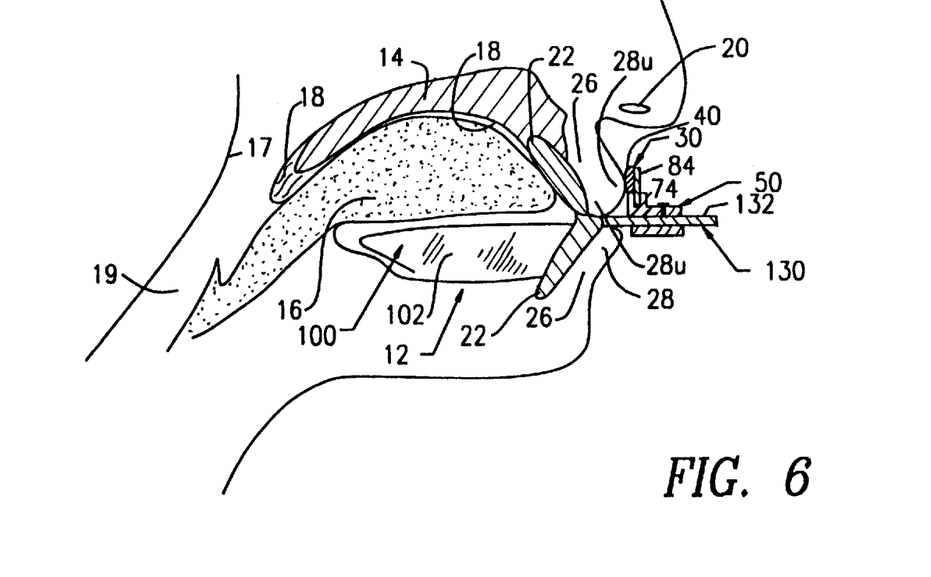
FIG. 6 is a cross-sectional view of the present invention showing the anti-snoring device in an operational mode and with the device inserted in the oral cavity having the user's tongue elevated to prevent snoring by a user, and showing the mandible advanced anteriorly by the device to prevent snoring by the user.

Thus, the oral shield 30 can be adjusted vertically, as well as horizontally with respect to the upper lip tissue 28u because of the adjustability both laterally and vertically of the horizontal section 52 and the telescoping vertical section 72, respectively, of connecting member 50, as shown in FIGS. 5 and 6 of the drawings.

The intraoral dental overlay 100 has a housing 102 which is substantially U-shaped in cross section and has an integrally attached anterior handle (extension member) 130 located at the bottom end of U-shaped housing 102, as shown in FIGS. 1 to 4 of the drawings. Dental overlay 100 includes an outer surface wall 104, and an inner surface wall 106 having an integrally attached outer perimeter wall 112 with an outer perimeter edge 114, and having an integrally attached inner perimeter wall 116 with inner upper and lower perimeter edges 118 and 120. The inner surface wall 106 is molded into a plurality of spaced-apart tooth-receiving areas 108 separated by occlusal ribs 110. The inner perimeter wall 116 and the inner upper perimeter edge 118 act as the lingual shelf portion 122 of the dental overlay 100. It is the lingual shelf portion 122 which acts as a support for the tongue 16 against the palate 18 of the mouth 26 of the user, as shown in FIG. 6 of the drawings. The lingual shelf portion 122 helps to prevent the act of snoring.

The anterior handle or extension member 130 includes an elongated strip section 138 formed of plastic having top and bottom wall surfaces 132 and 134 and a U-shaped perimeter edge 136. The horizontal section 52 of connecting member 50 may be slidably adjusted on strip section 138 of anterior handle 130, and is set in place by set screw 68, such that the oral shield is in a correction position for a comfortable placement by the user, as shown in FIGS. 5 and 6 of the drawings.

The dental overlay 100 is made from a flexible thermoplastic material (elastomeric resin) which is moldable after immersion in boiling water; such that the user may mold the dental overlay 100 to the shape of his or her lower jaw 12, perioral area 26 and lip area 28. Such moldable materials of construction may include ethyl vinyl acetate, methyl vinyl acetate, methyl acrylate, or other elastic resins which are softened and moldable in hot water and return to a hardened and stable form upon cooling to room temperature. The oral shield 30, the connecting member 50, and the dental overlay 100 with anterior handle 130 may be formed by an injection molding process.

DETAILED DESCRIPTION OF THE ALTERNATE EMBODIMENT

Figure 7:
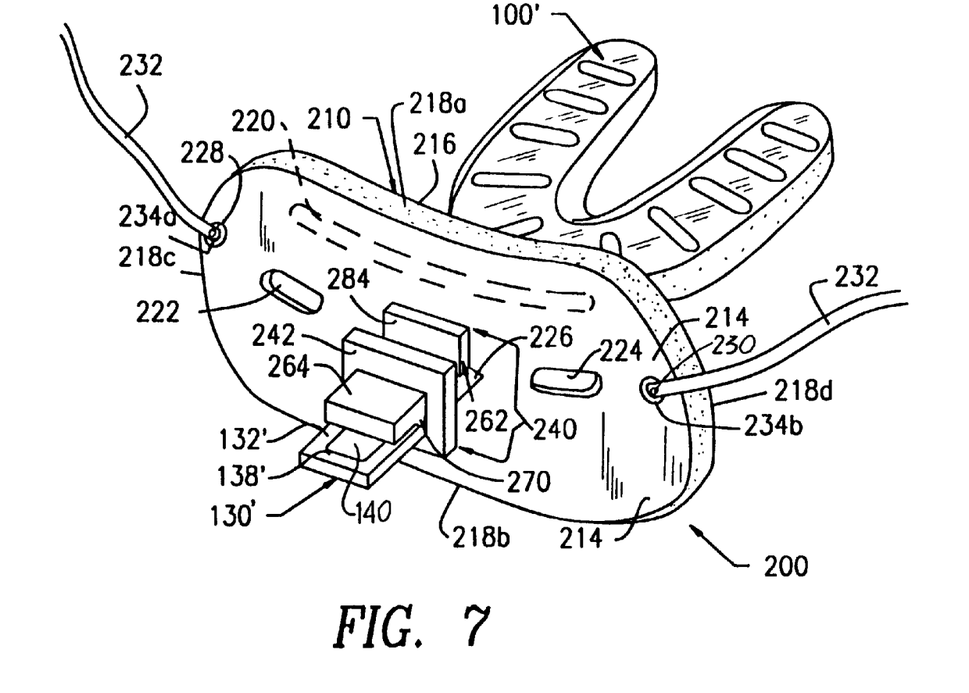
FIG. 7 is a front perspective view of an alternate embodiment of the present invention showing an anti-snoring device having an adjustable external oral shield with a removable retaining strap, a retention connecting member having a plurality of saw-tooth retention teeth, and an intraoral dental overlay with an anterior handle attached thereto, and in an assembled configuration.
Figure 8:
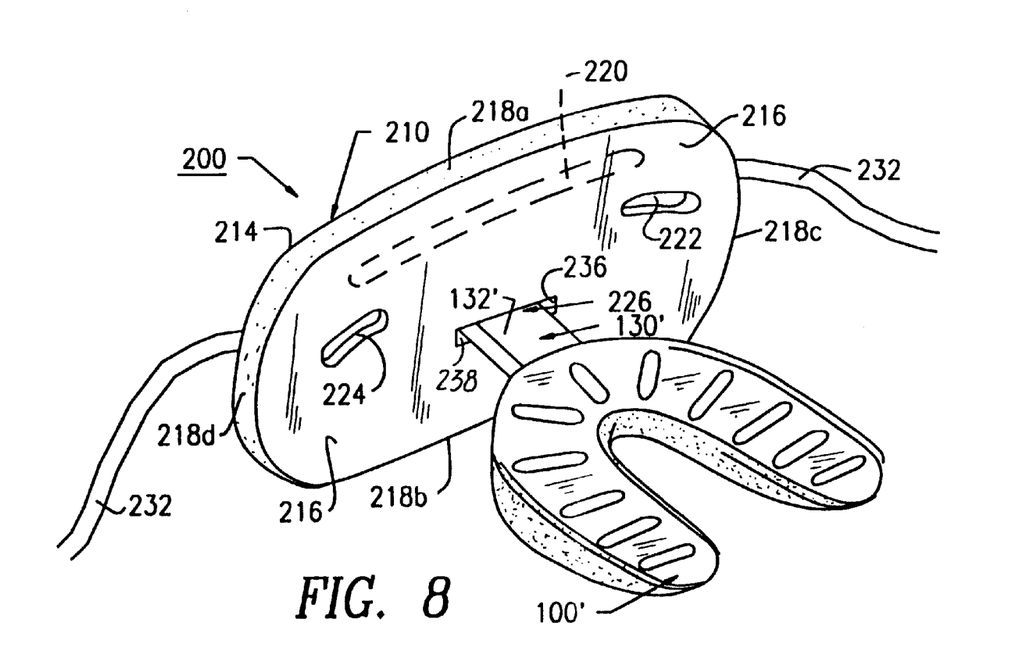
FIG. 8 is a rear perspective view of the alternate embodiment of the present invention showing an anti-snoring device having an adjustable external oral shield with a removable retaining strap, a retention connecting member having a plurality of saw-tooth retention teeth, and an intraoral dental overlay with an anterior handle attached thereto, and in an assembled configuration.
Figures 9, 10:
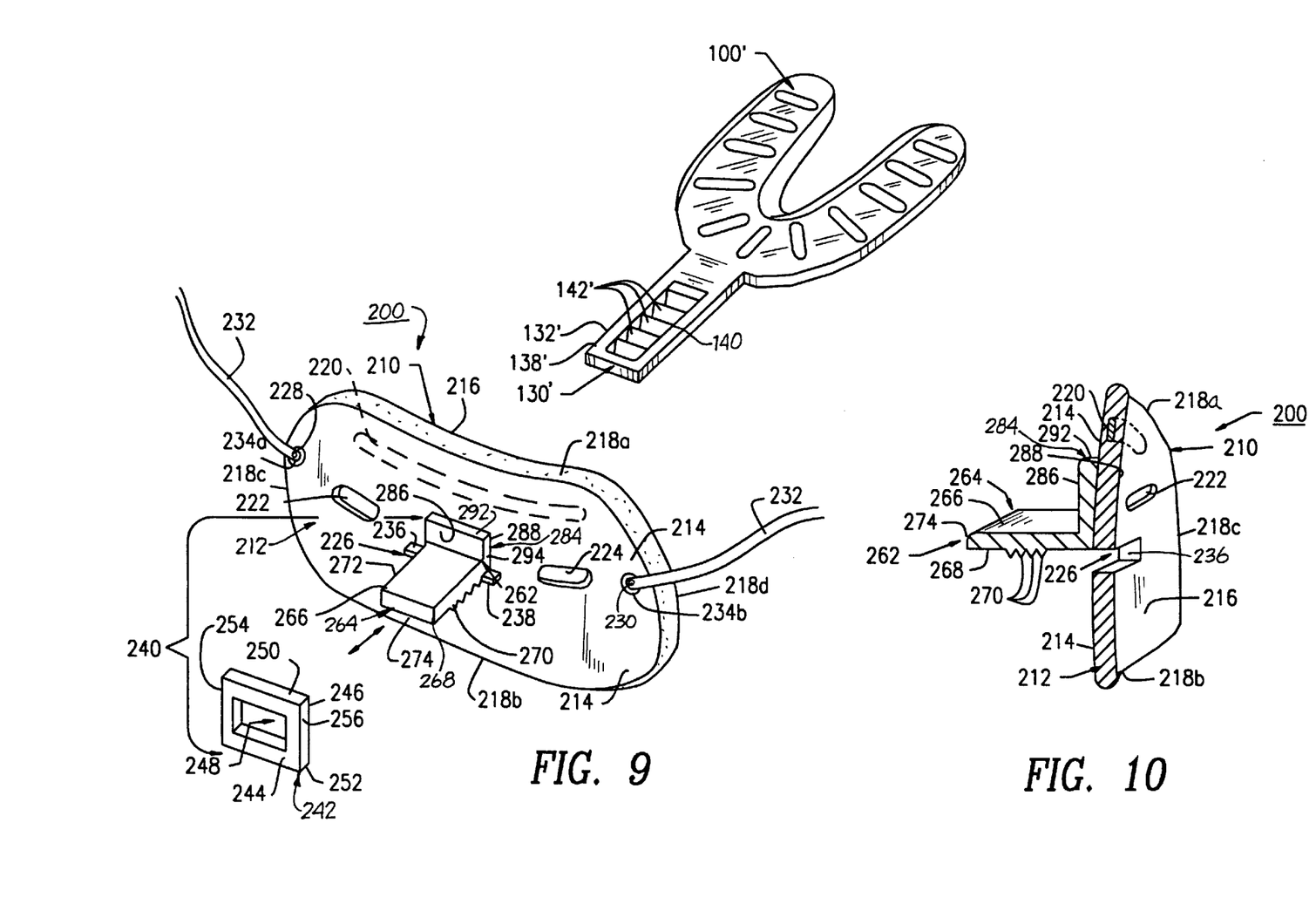
FIG. 9 is an exploded perspective view of the alternate embodiment of the present invention showing an anti-snoring device having an adjustable external oral shield with a removable retaining strap, a retention connection member having a plurality of saw-tooth retention teeth, and a intraoral dental overlay with an anterior handle attached thereto, and in an unassembled configuration.
FIG. 10 is a cross-sectional view of the anti-snoring device of the alternate embodiment of the present invention taken along lines 10—10 of FIG. 9 showing the oral shield with an interior metal strip, and the retention flange of the retention connecting member.

The anti-snoring device 200 and its component parts of the alternate embodiment of the present invention are represented in detail by FIGS. 7 through 10 of the drawings. The anti-snoring device 10 comprises an external, adjustable oral shield 210 being substantially elliptical and convex in shape; a retention connecting member 240 being substantially L-shaped in configuration; and an intraoral lower dental overlay 100' having an integrally attached anterior handle or extension member 130' as shown in FIG. 9.

Oral shield 210, as shown in FIGS. 7 to 10, includes an elastomeric material layer 212 having an outer surface wall 214, an inner surface wall 216, and side perimeter edges 218a, 218b, 218c and 218d. Elastomeric material layer 212 further includes an interior metal reinforcement strip or wire 220 being adjacent to the upper perimeter edge 218a, as shown in FIG. 10 of the drawings. In addition, oral shield 210 further includes two elliptical shaped breathing hole openings 222 and 224 for mouth breathing 26; and an extension member opening 226 for slidably receiving anterior handle 130' of dental overlay 100'. Extension member opening 226 is centrally located within oral shield 210 and breathing hole openings 222 and 224 are in-line and adjacent to each side 236 and 238 of extension member opening 226. Outer surface wall 212 includes a pair of strap retaining spherical tabs 228 and 230 being in-line and adjacent to breathing hole openings 236 and 238, respectively. Additionally, oral shield 210 also includes a removable retaining strap 232 having circular tab openings 234a and 234b to be received on spherical tabs 228 and 230, respectively. Retaining strap 232 is placed around the user's head, such that the anti-snoring device 200 may not be expelled by the patient involuntarily until he/she gets use to wearing the anti-snoring device 200. Retaining strap 232 is easily removed from tabs 228 and 230, once the user no longer expels the anti-snoring device 200 from the user's mouth 26.

The retention connecting member 240 includes a retention cuff 242 and a retention flange 262 for slidably receiving and holding in place extension member 130' and oral shield 210 in a predetermined position with respect to the user's mouth 26 and lip areas 28. Retention cuff 242 is substantially rectangular in shape and includes front and rear surface walls 244 and 246 having a retention opening 248 therebetween, top and bottom walls 250 and 252, and side walls 254 and 256. Retention flange 262 is substantially L-shaped in configuration and includes a horizontal member 264 integrally attached to a vertical member 284 at one end. Horizontal member 264 includes a top surface wall 266, a bottom surface wall 268 having a plurality of saw-tooth retention teeth 270 thereon and side surface walls 272, 274 and 276. Vertical member 284 includes a front surface wall 286, a rear surface wall 288 and side surface walls 290, 292 and 294. Rear surface wall 288 of the vertical member 284 is permanently connected to the outer surface wall 214 of oral shield 210, such that rear surface wall 288 is located above and adjacent to extension member opening 226 of oral shield 210, as shown in FIGS. 7 and 10 of the drawings.

Dental overlay 100' has an integrally attached anterior handle or extension member 130' which in the alternate embodiment 200 is exactly the same as the dental overlay 100 having an integrally attached anterior handle 130 of the preferred embodiment 10 except for a preformed plastic layer 140 having a plurality of saw-tooth retention teeth 142 which interfit with the saw-tooth retention teeth 270 of retention flange 262. The preformed plastic layer 140 having a plurality of saw-tooth retention teeth 142 is permanently attached to the top of surface wall 132' of extension member 130', as shown in FIGS. 7 and 9 of the drawings. After the retention teeth 142 have been interfitted at a pre-determined position with the retention teeth 270 of retention flange 262, the retention opening 248 of retention cuff 242 receives therein the combined structure of the retention flange 262 and the anterior handle 130'. Then retention cuff 262 locks in place the retention flange 262 to the anterior handle 130', as shown in FIGS. 7 and 8 of the drawings.

OPERATION OF THE PRESENT INVENTION

The anti-snoring device 10 of the present invention is designed and fabricated to be molded by the user without any assistance by a professional or a clinical laboratory. The initial step begins with the user immersing the dental overlay 100 and oral shield 30 into a container of boiling water. The dental overlay 100 and oral shield 30 are then moldable after immersion in boiling water, such that the aforementioned components 30 and 60 can be fitted by the user to give a comfortable and individualized fit. The molding act is performed by the user, by simply inserting the dental overlay 100 into the mouth 26, and placing the dental overlay 100 on the lower teeth 22 of lower jaw 12. The user then moves his/her lower and upper jaw 12 and 14, lips 28, and tongue 16 around; and bites with upper and lower teeth 22 and 24 into the outer and inner surface walls 104 and 106 of the softened elastomeric material which forms the dental overlay 100 to the individualized shape of the user's lower jaw area 12.

The next molding step is then effected by immersing the oral shield 30 in boiling water which allows this elastomeric component to become softened. The oral shield 30 is then taken out of the hot water and allowed to cool slightly before the user presses the oral shield 30 against his/or her upper lip 28u and perioral mouth tissues 26. The oral shield 30 is thus individualized to the user's upper lip 28u. The oral shield 30 via the connecting member 50 is then fitted onto the anterior handle 130 of the dental overlay 100 and slid along the handle strip 138 via the extension member opening 64 until the oral shield 30 meets the user's upper lip 28u. The anti-snoring device 10 is now ready for use to prevent snoring while sleeping.

When the user is ready to sleep the anti-snoring device is kept fully assembled. The dental overlay 100 is then inserted into the user's mouth 26 and placed on the lower teeth 22. The final act of adjustment occurs when the user slides the oral shield 30 towards the upper lip 28u via the connecting member 50 and at the same time the user postures the mandible (lower jaw) 12 forward. In so doing the tongue 16 is also postured forward, as depicted in FIG. 6 of the drawings. This posturing act carries the tongue 16 forward and away from the posterior wall 17 of the pharynx 19 which enables unobstructed respiration. Furthermore, the oral shield 30 acts as a lip seal so that the user is more apt to breath through the nasal passages 20 instead of the mouth 26, as shown in FIGS. 5 and 6. Once the anti-snoring device 10 is properly in place the user can sleep comfortably without any interference from the device 10 while sleeping. During sleep the dental overlay 100 supports the tongue and keeps it in engagement with the palate 18 to reduce the reverberation of the palate which causes snoring.

ADVANTAGES OF THE PRESENT INVENTION

Accordingly, the featured advantage of the present invention is that it provides for an anti-snoring device having an external oral shield and a dental overlay connected by an anterior handle to reduce or eliminate nocturnal snoring.

Another advantage of the present invention is that it provides for an anti-snoring device that is easily self-adaptable and which eliminates the need for professional and laboratory assistance or clinical fabrication.

Another advantage of the present invention is that it provides for an anti-snoring device that is fabricated from a thermoplastic material (elastomeric resin) which is moldable in shape to the user's lower jaw and perioral structure.

Another advantage of the present invention is that it provides for an anti-snoring device which is moldable after immersion in boiling water so that it can be adapted by the user to have a comfortable and individualized fit.

Another advantage of the present invention is that it provides for an anti-snoring device that has an adjustable external oral shield structure which reduces air turbulence within the user's mouth and thus promotes nasal breathing to prevent the act of snoring.

Another advantage of the present invention is that it provides for an anti-snoring device that has an adjustable external oral shield structure which acts as a lip seal, such that the user is more apt to breath through the nose instead of the mouth to prevent the act of snoring.

Another advantage of the present invention is that it provides for an anti-snoring device that has an adjustable external oral shield which is reduced in size so that the anti-snoring device is more comfortable, less bulky, more aesthetic looking and is more acceptable for use by a patient.

Another advantage of the present invention is that it provides for an anti-snoring device that has an adjustable external oral shield which only contacts the tissue below the nose and the inferior border of the upper lip, such that reduced size adjustable external oral shield still functions in preventing the lower jaw from moving inferiorly and posteriorly while the user is in the supine (sleeping) position.

Another advantage of the present invention is to provide an anti-snoring device that it provides for an adjustable external oral shield consisting of two different copolymer resin layers that have dissimilar melting points such that the softening and molding of the layered oral shield in boiling water does not distort the extension member and connecting member nor impair the adjustability of the oral shield relative to the connecting member.

Another advantage of the present invention is that it provides for an anti-snoring device that has an extension member, a connecting member, and a backing layer for the oral shield which will maintain their shapes and dimensions after submersion in boiling water and concurrently allow the elastomeric layer of the oral shield to be softened and molded to the user's external subnasal and lip tissue by manual manipulation of the oral shield without the immersion of the anti-snoring device into boiling water.

Another advantage of the present invention is that it provides for an anti-snoring device that has an adjustable external oral shield consisting of two layers, where the outer backing layer is made from a bendable metal or plastic; and the inner surface layer is made from an elastomeric material or a thermolabile copolymer resin. This construction allows the oral shield to be adapted to the upper lip contour of the user by bending and contouring with finger pressure instead of softening of the oral shield by the water boiling method.

Another advantage of the present invention is that it provides for an anti-snoring device that has an intra oral dental overlay structure which supports the tongue against the user's palate to keep the palate from reverberating during mouth breathing to prevent snoring by the user.

Another advantage of the present invention is that it provides for an anti-snoring device that includes an external oral shield in combination with an intraoral dental overlay connected by an anterior handle, such that the oral shield can be slidably adjusted on the handle by the user and which reduces the velocity of air flow through the mouth to reduce the reverberation of the palate to prevent the act of snoring.

A further advantage of the present invention is that it provides for an anti-snoring device which can be easily used, mass produced in an automated and economical manner, and is readily affordable by the user.

A still further advantage of the present invention is that it provides for adjustability of the oral shield along the handle of the dental overlay and allows the device to accommodate individual differences in the upper and lower jaw relationships of users. The user is able to adjust the entire anti-snoring device comfortably without sophisticated procedures and professional help.

An even further advantage of the present invention is that it provides for an adjustability of the oral shield along the telescoping vertical section of the connecting member, which allows vertical height adjustment relative to the oral shield thereby allowing the oral shield to accommodate individual differences beneath the user's nose and upper lip relationships. The user is able to adjust the entire anti-snoring device comfortably without sophisticated procedures and professional help.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An anti-snoring device comprising:
   a) a moldable dental overlay for covering the lower teeth of the user and for maintaining the tongue in contact with the palate to prevent air flow from causing the palate to reverberate during mouth breathing;
   b) an extension member fixedly connected to the front of said dental overlay;
   c) a moldable oral shield worn outside the mouth and being conformable to the user's upper lip for preventing the lower jaw from drifting inferiorly and posteriorly during sleep; and
   d) connecting means including a retention flange connected to said oral shield and a retention cuff for slidably receiving and holding said retention flange and said extension member in a co-linear relationship.

2. An anti-snoring device in accordance with claim 1, wherein said extension member includes a surface having ridges for co-acting with said retention flange having a surface with ridges.

3. An anti-snoring device in accordance with claim 1, wherein said retention flange has an L-shaped configuration, and includes a horizontal member and a vertical member.

4. An anti-snoring device in accordance with claim 1, wherein said retention cuff includes an opening for slidably receiving and holding said retention flange and said extension member in a co-linear relationship.

5. An anti-snoring device in accordance with claim 1, wherein said dental overlay is made of moldable thermoplastic or elastomeric resin materials.

6. An anti-snoring device in accordance with claim 5, wherein said thermoplastic or elastomeric resin materials are selected from the group consisting of ethyl vinyl acetate, methyl vinyl acetate, or methyl acrylate.

7. An anti-snoring device in accordance with claim 1, wherein said moldable oral shield, includes a moldable and conformable elastomeric layer.

8. An anti-snoring device in accordance with claim 7, wherein said elastomeric layer further includes an interior bendable metal strip or metal wire for bending and molding of said oral shield.

9. An anti-snoring device in accordance with claim 7, wherein said bendable metal strip or metal wire is made of aluminum, or steel or metallic alloy.

10. An anti-snoring device in accordance with claim 1, wherein said oral shield further includes a pair of retention tabs for holding a retaining strap to said oral shield.

11. An anti-snoring device in accordance with claim 1, wherein said dental overlay has an inner wall thicker than an outer wall, and said inner wall has a greater depth than said outer wall, said inner wall forming a part of a lingual shelf for supporting the tongue in contact with the palate.

12. An anti-snoring device in accordance with claim 1, wherein said dental overlay has a plurality of teeth-receiving areas separated by adjacent occlusal ribs.

13. An anti-snoring device in accordance with claim 1, wherein said dental overlay covers all lower teeth.

14. An anti-snoring device in accordance with claim 1, wherein said extension member is a flexible strip of plastic.

* * * * *